United States Patent [19]

Marki et al.

[11] 4,331,661

[45] May 25, 1982

[54] BOMBESIN ANALOGS

[75] Inventors: Walter E. Marki, Zurich, Switzerland; Marvin R. Brown; Jean E. F. Rivier, both of La Jolla, Calif.

[73] Assignee: The Salk Institute for Biological Studies, San Diego, Calif.

[21] Appl. No.: 193,621

[22] Filed: Oct. 3, 1980

[51] Int. Cl.$^3$ .................... A61K 37/00; C07C 103/52
[52] U.S. Cl. .............................. 424/177; 260/112.5 R
[58] Field of Search ................. 424/177; 260/112.5 R

[56] References Cited

U.S. PATENT DOCUMENTS 4,207,311  6/1980  Brown et al. ...................... 424/177

OTHER PUBLICATIONS

Roberto de Castiglione et al., "Peptides", 1972, pp. 463-466.
Chem. Abstr., 80, 1974, 96368b.
Chem. Abstr., 92, 140982w, 1980.
Chem. Abstr., 87, 1977, 168411e.
Rivier et al. Biochemistry, 17, (1978), 1766-1771.
Anastasi et al., Archives of Biochemistry and Biophysics, 148, 443-446, (1972).

Primary Examiner—Delbert R. Phillips
Attorney, Agent, or Firm—Fitch, Even, Tabin, Flannery & Welsh

[57] ABSTRACT

Peptides having thermoregulative and analgesic properties when administered to animals. The peptides are identified by the structure:

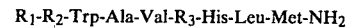

$R_1$-$R_2$-Trp-Ala-Val-$R_3$-His-Leu-Met-$NH_2$ wherein: $R_1$ is an acyl moiety selected from the group consisting of formyl, acetyl, propionyl, acrylyl and benzoyl; $R_2$ is selected from the group consisting of Gly and the D- and L-isomers of Ala, Asn, Gln, His, Leu, Met, Phe, Ser, Thr and Val; $R_3$ is selected from the group consisting of D-Ala and Gly. Intermediates of the peptides are also provided.

10 Claims, No Drawings

BOMBESIN ANALOGS

The invention described herein was made in the course of work under a grant or award from the Department of Health, Education and Welfare.

The present invention relates generally to peptides useful for thermoregulation of the body temperature of mammals, including humans. More particularly, the present invention is directed to methods for the reduction of core temperature in mammals or for inducing analgesia by the administration of particular peptides.

BACKGROUND OF THE INVENTION

The thermoregulation of body temperature of mammals is of great importance to the medical profession. Certain types of operations, particularly heart operations, are desirably performed with lowered body temperature. Certain physiological disorders result in malfunctioning of the thermoregulative function of the body resulting in increased and uncontrollable body temperatures. It would be desirable to provide a pharmaceutically effective composition which can be used to reduce the body temperature either from an undesirably high temperature or in preparation for medical treatment.

The tridecapeptide, neurotensin, has been isolated and characterized from bovine hypothalamus. Neurotensin has the structure:

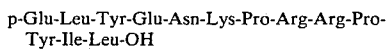

p-Glu-Leu-Tyr-Glu-Asn-Lys-Pro-Arg-Arg-Pro-Tyr-Ile-Leu-OH

Neurotensin has been reported to have a body temperature-lowering effect; G. Bissette et al, *Nature* 262: 607 (1976). In the studies reported in the G. Bissette et al article, neurotensin given intracisternally but not intravenously, produced a lowering of basal body temperature of mice at room temperature or exposed to cold (4° C.). However, the body temperature lowering effect of neurotensin is not sufficient for practical pharmaceutical and operative use.

U.S. Pat. No. 4,207,311, issued June 10, 1980 to Marvin R. Brown, et al. discloses the structure of bombesin and other related peptides which have been isolated from the skin of several anuran species. Amphibian bombesin has the formula:

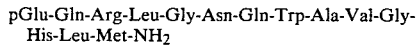

pGlu-Gln-Arg-Leu-Gly-Asn-Gln-Trp-Ala-Val-Gly-His-Leu-Met-NH$_2$

The patent discloses that the administration of bombesin to mammals, including humans, can be used for reducing the body temperature of the mammal as well as for inducing analgesia. The patent also discloses several analogs of bombesin which exhibit certain analgesic and thermoregulative effects in mammals including the octapeptide D-pGlu-Trp-Ala-Val-D-Ala-His-Leu-Met-NH$_2$. Although this octapeptide is more potent than neurotensin, it is less potent than bombesin, and more potent analogs having these properties would be of great value.

SUMMARY OF THE INVENTION

Octapeptides have been synthesized which are very substantially more potent than neurotensin and which have potencies substantially equal to or significantly greater than bombesin. These octapeptides are generally characterized by their resemblance to the eight-member fragment of bombesin at the C-terminal end thereof, sometimes referred to as amphibian bombesin residues 7–14, or $BN_a(7-14)$. More specifically, the amino acid residue at the N-terminal has its α-amino group acylated with an acyl moiety that is either formyl, acetyl, propionyl, acrylyl or benzoyl, and the particular amino acid residue in this position can be the L- or D-isomer of one of a large number of naturally occurring amino acids. In addition, the amino acid residue in the 5-position of the octapeptide can be either Gly or D-Ala.

DETAILED DESCRIPTION OF THE PREFERRED EMBODIMENTS

The present invention provides peptides which when administered to mammals, including humans, in an effective therapeutic amount, will (1) lower body temperature, (2) cause a rise in plasma glucose and (3) induce analgesia. These peptides are octapeptides which are analogs of $BN_a(7-14)$. The N-terminal of the octapeptide contains the residue of a naturally occuring amino acid wherein the α-amino group has been acylated. Either the D- or L-isomeric form of the amino acid can be used, and the L- form of the amino acid is intended herein unless the D- form is expressly indicated. The amino acid can be any which is sterically and functionally suitable and does not detract from the improved properties exhibited by this class of acylated octapeptides. Preferably, the amino acid residue at the N-terminal is Gly, Ala, Asn, Gln, His, Leu, Met, Phe, Ser, Thr or Val. The remaining seven members of the chain are substantially the same as the C-terminal end of bombesin; however, D-Ala can be substituted for Gly.

The peptides of the invention are identified by the structure: $R_1$-$R_2$-Trp-Ala-Val-$R_3$-His-Leu-Met-NH$_2$ wherein: $R_1$ is an acyl moiety selected from the group consisting of formyl, acetyl, propionyl, acrylyl and benzoyl; $R_2$ is selected from the group consisting of Gly and the D- and L-isomers of Ala, Asn, Gln, His, Leu, Met, Phe, Ser, Thr and Val; $R_3$ is selected from the group consisting of D-Ala and Gly.

The peptides of the present invention can be synthesized by a solid phase technique using a chloromethylated resin, a methylbenzhydrylamine resin (MBHA) or a benzhydrylamine (BHA) resin. The synthesis is conducted in a manner to stepwise add the amino acids in the chain in the manner set forth in detail in U.S. Pat. Nos. 4,207,311 and 4,211,693, the disclosures of which are incorporated herein by reference. Side-chain protecting groups, as are well known in the art, are preferably added to Ser, Thr, His, Asn or Gln (if one of these is used in the 1-position) and to Trp and His before these amino acids are coupled to the chain being built up upon the resin. Such a method provides the fully protected intermediate peptidoresin. The fully protected peptide can be cleaved from the chloromethylated resin support by ammonolysis, as is well known in the art, to yield the fully protected amide intermediate.

The intermediates of the invention may be represented as:

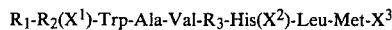

$R_1$-$R_2(X^1)$-Trp-Ala-Val-$R_3$-His$(X^2)$-Leu-Met-$X^3$ wherein: the acyl moiety $R_1$ may serve as the protecting group for the α-amino group of $R_2$ or a well known α-amino protecting group may be present.

$X^1$ is hydrogen or a protecting group for the side chain functional group of the amino acid $R_2$, i.e., when $R_2$ is Asn or Gln, $X^1$ is either hydrogen or xanthyl (Xan); when $R_2$ is His, $X^1$ is a protecting group for the imidazole nitrogen selected from the group consisting of
p-toluenesulfonyl(Tos), benzyl, trityl,
t-butyloxycarbonyl(Boc), benzyloxycarbonyl,
2,4-dinitrophenyl(Dnp),
2,2,2-trifluoro-1-benzyloxycarbonylaminoethyl, and
2,2,2-trifluoro-1-tert-butyloxycarbonylaminoethyl; and when $R_2$ is Ser or Thr, $X^1$ is a protecting group for the alcoholic hydroxyl group of Ser or Thr and is selected from the group consisting of acetyl, benzoyl, tetrahydropyranyl, tert-butyl, trityl, benzyl and 2,6-dichlorobenzyl.

$X^2$ is a protecting group for His as defined in respect of $X^1$.

$X^3$ is selected from —O—CH$_2$—[resin support] and —NH—[resin support].

The criterion for selecting a side chain protecting group for $X^2$ is that the protecting group should be stable to the reagent under the reaction conditions selected for removing the α-amino protecting group at each step of the synthesis. The preferred α-amino protecting group is Boc. Any protecting group must not be split off under coupling conditions and must be removable upon completion of the synthesis of the desired amino acid sequence under reaction conditions that will not alter the peptide chain.

When the $X^3$ group is —O—CH$_2$—[resin support], the ester moiety of one of the many functional groups of the polystyrene resin support is being represented. When the $X^3$ group is —NH—[resin support], an amide bond connects Met to a BHA resin or to a methyl BHA resin.

$R_1$ is acetyl, formyl, acrylyl, propionyl or benzoyl and may be employed as the protecting group for the α-amino group of $R_2$, in which case it is accordingly added to the amino acid before it is coupled to the peptide chain. Alternatively, a reaction is preferably carried out with the peptide on the resin, e.g. reacting with acetic acid in the presence of dicyclohexyl carbodiimide (DCC) or with acetic anhydride, to replace Boc which was initially used as the protecting group.

Deprotection of the peptide as well as cleavage of the peptide from a BHA resin or methyl BHA resin takes place at 0° C. with hydrofluoric acid (HF). Anisole and methylethyl sulfide are added to the peptide prior to treatment with HF. After the removal of HF, under vacuum, the cleaved, deprotected peptide-resin mixture is treated with ethyl ether, filtered, extracted in dilute acetic acid and lyophilized.

Purification of the peptide is effected by ion exchange chromatography on a CMC column, followed by partition chromatography using the elution system: n-butanol; glacial acetic acid; water (4:1:5 volume ratio) on a column packed with Sephadex G 25F.

The peptides of the invention are significantly more effective than neurotensin to produce hypothermia when the peptides are administered intracisternally in a mammal at a level of from about 5 to about 5000 nanograms per kilogram of body weight. The peptides are not effective to produce hypothermia when administered intravenously or subcutaneously even when administered at dosage levels 10 times the effective dosage level administered intracisternally. At the above indicated dosage level and route of administration, the peptides of the invention also have a strong analgesic function.

The following examples further illustrate various features of the invention but are intended to in no way limit the scope of the invention which is defined in the appended claims.

EXAMPLE

The following peptides having the formula $R_1$-$R_2$-Trp-Ala-Val-$R_3$-His-Leu-Met-NH$_2$ are prepared by the solid phase procedure referred to above.

TABLE I

| PEPTIDE | $R_1$ | $R_2$ | $R_3$ |
|---|---|---|---|
| 1 | Ac | His | Gly |
| 2 | " | Ala | D-Ala |
| 3 | " | D-Gln | D-Ala |
| 4 | " | Ala | Gly |

For purposes of an example, a representative solid phase synthesis of Peptide No. 1 above, which is referred to as [Ac-His$^7$]-BN$_a$(7–14), is set forth hereinafter. This peptide has the following formula:

Ac-His-Trp-Ala-Val-Gly-His-Leu-Met-NH$_2$.

A BHA resin is used, and Boc-protected Met is coupled to the resin over a 2-hour period in CH$_2$Cl$_2$ using a 3-fold excess of Boc derivative and DCC as an activating reagent. The methionine residue attaches to the BHA resin by an amide bond.

Following the coupling of each amino acid residue, washing, deblocking and coupling of the next amino acid residue are carried out in accordance with the following schedule using an automated peptide synthesizer (Beckman Model 990B) and beginning with 5 grams of resin:

| STEP | REAGENTS AND OPERATIONS | MIX TIMES MIN. |
|---|---|---|
| 1 | CH$_2$Cl$_2$ wash-80 ml. (2 times) | 3 |
| 2 | Methanol (MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$-70 ml. (2 times) | 10 |
| 5 | CH$_2$Cl$_2$ wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30–300 |
| 10 | MeOH wash-40 ml. (2 times) | 3 |
| 11 | TEA 12.5 percent in CH$_2$Cl$_2$-70 ml. (1 time) | 3 |
| 12 | MeOH wash-30 ml. (2 times) | 3 |
| 13 | CH$_2$Cl$_2$ wash-80 ml. (2 times) | 3 |

After step 13, an aliquot is taken for a ninhydrin test: if the test is negative, go to step 1 for coupling of the next amino acid; if the test is positive or slightly positive, go back and repeat steps 9 through 13.

The above schedule is used for coupling of each of the amino acids of the peptide of the invention after the first amino acid has been attached, except for Leu and Trp which were dissolved in about 10% DMF/CH$_2$Cl.

N<sup>α</sup> Boc protection is used for each of the remaining amino acids throughout the synthesis. The side chain of His is protected with Tos. N-Boc-Tos-L-His is introduced as the final amino acid which, after deblocking, is easily acylated with acetic anhydride.

The cleavage of the peptide from the resin and complete deprotection of the side chains take place very readily at −20° C. for 30 minutes followed by 45 minutes at 0° C. with 10 ml. of HF per gram of resin-peptide. Anisole (1.5 ml) and methylethyl sulfide (0.4 ml) are added as scavengers, per gram of peptide resin, prior to HF treatment. After the removal of HF under vacuum, the resin is washed with ethyl ether, extracted with 50% acetic acid, and lyophilized to provide a crude peptide powder.

Purification of the peptide is then effected by ion exchange chromatography on CMC (Whatman CM 52, using a gradient of 0.01 to 0.25 NH$_4$OAc in 50/50 methanol/water) followed by partition chromatography in a gel filtration column on Sephadex G 25F using the elution system: n-butanol; glacial acetic acid; water (4:1:5-volume ratio). This may be followed by semi-preparative RP-HPLC.

Following RP-HPLC purification, testing shows the purity is greater than 98%, which means that, under the conditions, no detectable impurity was observed. Examination shows that the octapeptide has an optical rotation of $[\alpha]_D^{23} = -48° \pm 1°$ (C=0.5 in 1 N acetic acid). Peptides Nos. 2–4 are similarly synthesized, purified and tested and exhibit the specific optical rotations as follows:

Peptide No. 2-$[\alpha]_D^{23} = -47.3° \pm 1°$ (C-0.5 in 1% HOAc)

Peptide No. 3-$[\alpha]_D^{23} = -30° \pm 1°$ (C=0.3 in 1% HOAc)

Peptide No. 4-$[\alpha]_D^{23} = -57° \pm 1°$ (C=0.5 in 1% HOAc)

Amino acid analyses of the purified materials show the expected ratios for the different amino acids within 10% of unity.

Active esters can be used in solid phase synthesis, and the classical method of synthesis can also be used to prepare the peptides of the invention.

The thermoregulative properties of the peptides were determined as follows:

Male Sprague-Dawley-CD rats weighing 180–200 grams each were housed in temperature and humidity controlled quarters. The rats were fed a standard rat food ration and tap water ad libitum. After being anesthetized with ether, peptides were injected into the cisterna magna of the brain of each rat. The peptides were dissolved in artificial CSF or distilled water. Ten microliters of a peptide solution containing the specified amounts of the peptide were injected. Immediately following the injection, the animals were transferred to a cold room maintained at 4° C. Rectal temperatures were recorded with a thermo-probe at 60 minutes following injection. All experiments were carried out in a randomized block design. Following analyses of variance, differences between groups were determined by the multiple range test of Dunnet and Duncan using the computer program Exbiol.

Table II shows the effects of the four peptides on core temperature, compared with BN$_a$ and neurotensin, 60 minutes following injection.

TABLE II

| PEPTIDE | DOSAGE | CORE TEMPERATURE °C. |
|---|---|---|
| Control | — | 36.5° |
| Neurotensin | 100 μg. | 34° |
| Bombesin | 7 picomoles | 34.7° |
|  | 20 picomoles | 33.8° |
|  | 70 picomoles | 33° |
|  | 7 nanomoles | 32.1° |
| No. 1 | 10 picomoles | 34.3° |
|  | 100 picomoles | 33.2° |
|  | 1 nanomole | 32.6° |
| No. 2 | 10 picomoles | 34.3° |
|  | 100 picomoles | 31.9° |
|  | 1 nanomole | 30.4° |
| No. 3 | 10 picomoles | 32.3° |
|  | 100 picomoles | 31.9° |
| No. 4 | 10 picomoles | 35.1° |
|  | 100 picomoles | 33.2° |

Following the 60 minute measurement of core temperature, the rats were rapidly decapitated, blood was collected and plasma levels of glucose were determined using a Beckman glucose analyzer. The results in causing a rise in plasma glucose relative to Bombesin are set forth hereinafter in Table III.

TABLE III

| PEPTIDE | POTENCY (Plasma Glucose) |
|---|---|
| Bombesin | 100 |
| No. 1 | 100 |
| No. 2 | 150 |
| No. 3 | 150 |
| No. 4 | 40 |

Analgesic potency of each of these peptides is also assessed by the "tail flick" test with mice. After intravenous or subcutaneous administration of the peptides, tails of mice are placed in a 58° C. water bath. In the absence of an analgesic, the mice "flick" their tails from the water. The peptides are considered to be more potent than commonly administered analgesics because small amounts of the peptides give such an analgesic effect.

The peptides may also be prepared for administration intravenously or subcutaneously in the form of a pharmaceutically acceptable nontoxic salt, such as an acid-addition salt. Illustrative of pharmaceutically acceptable, nontoxic salts of peptides are hydrochloride, hydrobromide, sulfate, phosphate, maleate, acetate, citrate, benzoate, succinate, malate, ascorbate, and the like.

These peptides can be administered to mammals intracisternally, intravenously or subcutaneously. Effective dosages will vary with the form of administration and the particular species of mammal being treated.

Although the invention has been described with regard to its preferred embodiments, it should be understood that changes and modifications as would be obvious to one having the ordinary skill in this art may be made without departing from the scope of the invention which is set forth in the claims which are appended hereto.

What is claimed is:

1. A peptide or a nontoxic salt thereof, said peptide having the formula:

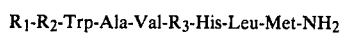

R$_1$-R$_2$-Trp-Ala-Val-R$_3$-His-Leu-Met-NH$_2$ wherein: $R_1$ is an acyl moiety selected from the group consisting of formyl, acetyl, propionyl, acrylyl and benzoyl; $R_2$ is selected from the group consisting of Gly and the D- and L-isomers of Ala, Asn, Gln, His, Leu, Met, Phe, Ser, Thr and Val; $R_3$ is selected from the group consisting of D-Ala and Gly.

2. A peptide in accordance with claim 1 wherein $R_1$ is acetyl.

3. A peptide in accordance with claim 2 wherein $R_2$ is His.

4. A peptide in accordance with claim 3 wherein $R_3$ is Gly.

5. A peptide in accordance with claim 2 wherein $R_2$ is Ala.

6. A peptide in accordance with claim 5 wherein $R_3$ is D-Ala.

7. A peptide in accordance with claim 2 wherein $R_2$ is D-Gln.

8. A peptide in accordance with claim 7 wherein $R_3$ is D-Ala.

9. A peptide in accordance with claim 1 wherein $R_1$ is acrylyl.

10. A method for reducing the body temperature of mammals comprising administering an effective amount of a peptide, or a nontoxic salt thereof, to a mammal, said peptide having the formula:

$$R_1\text{-}R_2\text{-}Trp\text{-}Ala\text{-}Val\text{-}R_3\text{-}His\text{-}Leu\text{-}Met\text{-}NH_2$$

wherein: $R_1$ is an acyl moiety selected from the group consisting of formyl, acetyl, propionyl, acrylyl and benzoyl; $R_2$ is selected from the group consisting of Gly and the D- and L-isomers of Ala, Asn, Gln, His, Leu, Met, Phe, Ser, Thr and Val; $R_3$ is selected from the group consisting of D-Ala and Gly.

* * * * *